(12) United States Patent
Yu

(10) Patent No.: US 7,657,444 B2
(45) Date of Patent: Feb. 2, 2010

(54) DISTANCE-TREATMENT THROUGH PUBLIC NETWORK

(76) Inventor: Qi Yu, 15332 E. Valley Blvd., City of Industry, CA (US) 91745

( * ) Notice: Subject to any disclaimer, the term of this patent is extended or adjusted under 35 U.S.C. 154(b) by 845 days.

(21) Appl. No.: 09/978,221

(22) Filed: Oct. 16, 2001

(65) Prior Publication Data

US 2003/0074227 A1    Apr. 17, 2003

(51) Int. Cl.
*A61B 5/00* (2006.01)

(52) U.S. Cl. .......................... 705/3; 128/897; 600/300; 600/407; 600/509; 600/528; 600/529; 604/66; 607/2; 607/50; 607/66; 607/88; 704/270; 705/2

(58) Field of Classification Search ............... 705/2, 705/3; 607/50, 2, 88, 66; 600/528, 300, 600/509, 407, 529; 604/66; 128/897; 704/270
See application file for complete search history.

(56) References Cited

U.S. PATENT DOCUMENTS

| | | | | |
|---|---|---|---|---|
| 4,446,870 A * | 5/1984 | Wing | ............................ | 607/72 |
| 4,556,064 A * | 12/1985 | Pomeranz et al. | ............. | 607/66 |
| 4,933,873 A * | 6/1990 | Kaufman et al. | ............ | 704/270 |
| 5,036,462 A * | 7/1991 | Kaufman et al. | ............ | 600/300 |
| 5,038,800 A * | 8/1991 | Oba | ............................ | 600/509 |
| 5,410,471 A * | 4/1995 | Alyfuku et al. | ............. | 600/300 |
| 5,416,804 A * | 5/1995 | Khaled et al. | ................ | 375/341 |
| 5,549,117 A * | 8/1996 | Tacklind et al. | ............. | 600/529 |
| 5,558,638 A * | 9/1996 | Evers et al. | .................... | 604/66 |
| 5,735,285 A * | 4/1998 | Albert et al. | ................ | 600/509 |
| 6,022,315 A * | 2/2000 | Iliff | ............................ | 600/300 |
| 6,039,688 A * | 3/2000 | Douglas et al. | ............. | 600/300 |
| 6,221,095 B1 * | 4/2001 | Van Zuylen et al. | ........... | 607/88 |
| 6,237,603 B1 * | 5/2001 | Mendell | ..................... | 128/897 |
| 6,264,614 B1 * | 7/2001 | Albert et al. | ................ | 600/528 |
| 6,522,929 B2 * | 2/2003 | Swing | ......................... | 607/50 |
| 2001/0031989 A1 * | 10/2001 | Swing | ............................ | 607/2 |
| 2001/0034617 A1 * | 10/2001 | Kimata | ........................ | 705/3 |
| 2001/0039503 A1 * | 11/2001 | Chan et al. | ..................... | 705/2 |
| 2002/0065682 A1 * | 5/2002 | Goldenberg | ................... | 705/2 |
| 2002/0120187 A1 * | 8/2002 | Eiffert et al. | ................ | 600/407 |
| 2003/0023129 A1 * | 1/2003 | Bologna | ........................ | 600/9 |

* cited by examiner

*Primary Examiner*—C. Luke Gilligan
*Assistant Examiner*—Dilek B Cobanoglu
(74) *Attorney, Agent, or Firm*—Raymond Y. Chan; David and Raymond Patent Firm

(57) ABSTRACT

A method and system of providing biological distance-treatment through a public network includes at least a treatment instrument which is electrically connected with an information connection system for providing a treatment for a registered user, wherein a treatment information data package sent from a service provider via the information connection system through the public network to provide digital treatment signals to control the treatment, wherein the treatment information data package is selected from the treatment information database based on a treatment request sent from the information connection system to the service provider and the health information profile of the registered user in the service provider.

15 Claims, 2 Drawing Sheets

DISTANCE-TREATMENT THROUGH PUBLIC NETWORK

BACKGROUND OF THE PRESENT INVENTION

1. Field of Invention

The present invention relates to health treatments, and more particularly to a method and system of a biological distance-treatment through the public network such as Internet.

2. Description of Related Arts

Biological treatments include medical treatment and health treatment such as physical treatment. It is well known that a human body is very reactive with respect to the changes of environment.

A living being will feel uncomfortable and sickness when its body suffers a disease or is injured. When a living body infects harmful bacteria or virus, the immune system of the living body will cause illness, uncomfortable and painful feels to the diseased body, such as ache, fever and dizzy, that is an alarm system to alert that the diseased body is not properly functioned and has a risk of having serious damages.

When a human being gets sick, the first issue is to see a doctor and make a diagnosis of what is his or her disease, so that a corresponding medical treatment can be given to the patient. To take medicine is the most common way of medical treatment in both the Western and oriental medical sciences. For some known diseases, such as the sprain and paralysis, physical treatment may be a more appropriate treatment to regain health. Other than medicines, acupuncture is a famous and effective oriental medical treatment, wherein specific acupoints of the human body are stimulated by specific acupuncture needles with a predetermined way or by electric pulses with predetermined energy magnitude and frequency for a certain time period. Foot-massage is another well-known oriental medical treatment that is proved especially effective to a lot internal organ diseases.

Some health problems, such as emotional depression, abnormal blood pressure, over weight, stomach ache, headache, muscle ache after exercise, and constipation, cause no immediate injury or disease to the human body but can be improved by certain respective health treatments. The followings are examples of some common health treatments:

(1) It is a pretty effective health treatment for improving your visual ability by viewing far and green field as much as possible.
(2) It is also well known that music can affect the metabolism and mental condition of a human body. The pop music may energize a teenager while it may only annoy a senior. When a person has a bad mood or a nervous and anxiety mind, it is proved that a pleasing or sweet-sounding melody can relax you.
(3) Also, by wearing a brass made bracelet, a golfer can substantially reduce his or her muscle ache by supplying brass ions to the muscle tissues.
(4) When your muscle feels tired, the best physical treatment is to massage the ached muscle. When you can't have a hand massage, it is well known that an alterative treatment is to massage your muscle with appropriate electric pulses.

In view of the above typical examples of simple health treatment for human, the treatment itself basically has no harm to a human body but provides effective therapeutic effect when it is applied appropriately.

Theoretically speaking, a living body is an organic reactor of chemical reactions (such as the digest system and muscular actions) and electric circuits (such as the nervous system) responsive to the environment and inputs. The gene of each living cell is a preset program controlling the reaction of the cell with the chemicals and information inputted into the living body. The ears, eyes, mouth, nose, skin, and intuition are known "input devices" of a human body, by which we can input new information through listening, seeing, smelling, tasting, feeling, and intuiting, and input water and nutrition by means of drinking and eating.

After you input food by eating and drinking through your mouth, you digest the food, through a series of chemical reactions, into nutrition that your cells absorb to produce energy and excreta. You may also input medical drugs into your body through your mouth to cure your disease or to help you to kill the infected bacteria. The mouth is the most important "input device" of a human body.

When you hear something you like, such as your favor music, your body reacts positively to have a better mood. However, if you hear something you don't like, you may lose your temper. Because a human body is proved to automatically react with respect to different specific sound waves. When you see a tragedy screen, your body reacts to have a sad mood. Also, when a young man sees a sexy woman, his body may automatically react to have a faster heartbeat and excitement. Moreover, all human beings like to smell fragrance but hate to smell deodorant. In other words, the sense organs, i.e. eyes, ears, nose and tongue, are other important "input devices" of a human body.

Even our skin is a kind of "input device" that is good at sensing the changes of the environment, such as the temperature, humidity and pressure. During a hot spring treatment, our body reacts accordingly, such as enhancing the blood circulation, when our skin senses the high temperature and absorbs the sulphur content of the hot spring.

Besides, the above mentioned sense organs, the oriental medical science proved that a human body contains a plurality of acupoints each of which functions as a switch of a specific organ or a body function. When a specific acupoint is stimulated by an acupuncture needle or electric pulses, the body will reacts accordingly. There are still a lot of things in earth that we can't see, smell, hear, sense, and feel, such as electromagnetic waves, far infrared rays, microwaves, and etc., but our body will be affected and react therewith when our body is exposed in such environment.

Therefore, all biological treatments are different predesigned methods for affecting and controlling a human body to react in such a way that can cure the diseases or improve the health condition.

Of course, when you have a disease, you should see a doctor for a diagnosis and medical treatment. However, unless your disease is serious enough that the hospital accepts you to stay there 24 hours a day, the doctor will not take care you all the time. For example, if a person would like to receive an electrical acupuncture treatment to heal his constipation problem, he or she must visit the oriental doctor and can only receive the treatment in the clinic. It is because even though the electric pulse is so weak that would not cause injury, it is required to stimulate the right acupoint with a predetermined intensity of electric pulses at predetermined frequency in order to obtain the best effect, or otherwise there is no effect at all if you don't know where and which is the specific acupoint to be stimulated. Therefore, there is no way for a person to receive such treatment at home or whenever he or she has time after work.

SUMMARY OF THE PRESENT INVENTION

It is a main objective of the present invention to provide a distance-treatment through public network, which enables a user to receive biological treatment at his or her own place under the professional instruction.

It is another objective of the present invention to provide a distance-treatment through public network, wherein the treatment instrument of the user is directly controlled by a service provider through the Internet according to the diagnosis provided by the user or the personal health condition inputted by the user.

It is another objective of the present invention to provide a distance-treatment through public network wherein the live-reaction information of the user during treatment is fed back to the service provider through the public network so that the service provider may adjust the user's treatment instrument through the public network correspondingly.

It is another objective of the present invention to provide a distance-treatment through public network wherein the user can receive health treatment at home or even during business hours whenever the user's computer connected with the treatment instrument is online, so that the user saves the time to make appointment and see the doctor at specific time. This is especially true for those who have been suffering chronic illness.

It is a further objective of the present invention to provide a distance-treatment through public network, wherein the user can receive respective medical treatment at the user's own place after the user inputs his or her medical diagnosis through the public network.

It is a further objective of the present invention to provide a distance-treatment through public network, wherein different users who registered with different passwords and user IDs can use the same information connection system and treatment instrument to receive different treatments.

It is a further objective of the present invention to provide a distance-treatment through public network, wherein a decoder is connected between the information connection system and the treatment instrument, so as to decode the digital signals received from the information connection system to readable analog signals for the treatment instrument.

In order to accomplish the above objective, the present invention provides a distance-treatment through public network, which comprises the steps of:

(a) providing a treatment information database and a health information database in a service provider, wherein the treatment information database includes a plurality of treatment information with respect to different kinds of classified health problem and the health information database includes health information profiles established for the registered users respectively, wherein each of the health information profiles includes a personal general information and a personal health information of the respective registered user;

(b) providing a treatment instrument for each registered user to connect with an information connection system arranged to communicate with the service provider through a public network;

(c) verifying the registered user and admitting the registered user to login the health information profile of the registered user and to request a distance-treatment;

(d) receiving a treatment request from the information connection system of the registered user through the public network;

(e) based on the treatment request and the health information profile of the registered user, selecting a treatment information data package from the treatment information database and sending digital treatment signals of the treatment information data package to the information connection system of the registered user through the public network; and (f) decoding the digital treatment signals received into analog treatment signals to operate and control the treatment instrument to work on the registered user.

DETAILED DESCRIPTION OF THE PREFERRED EMBODIMENT

Figure 1:
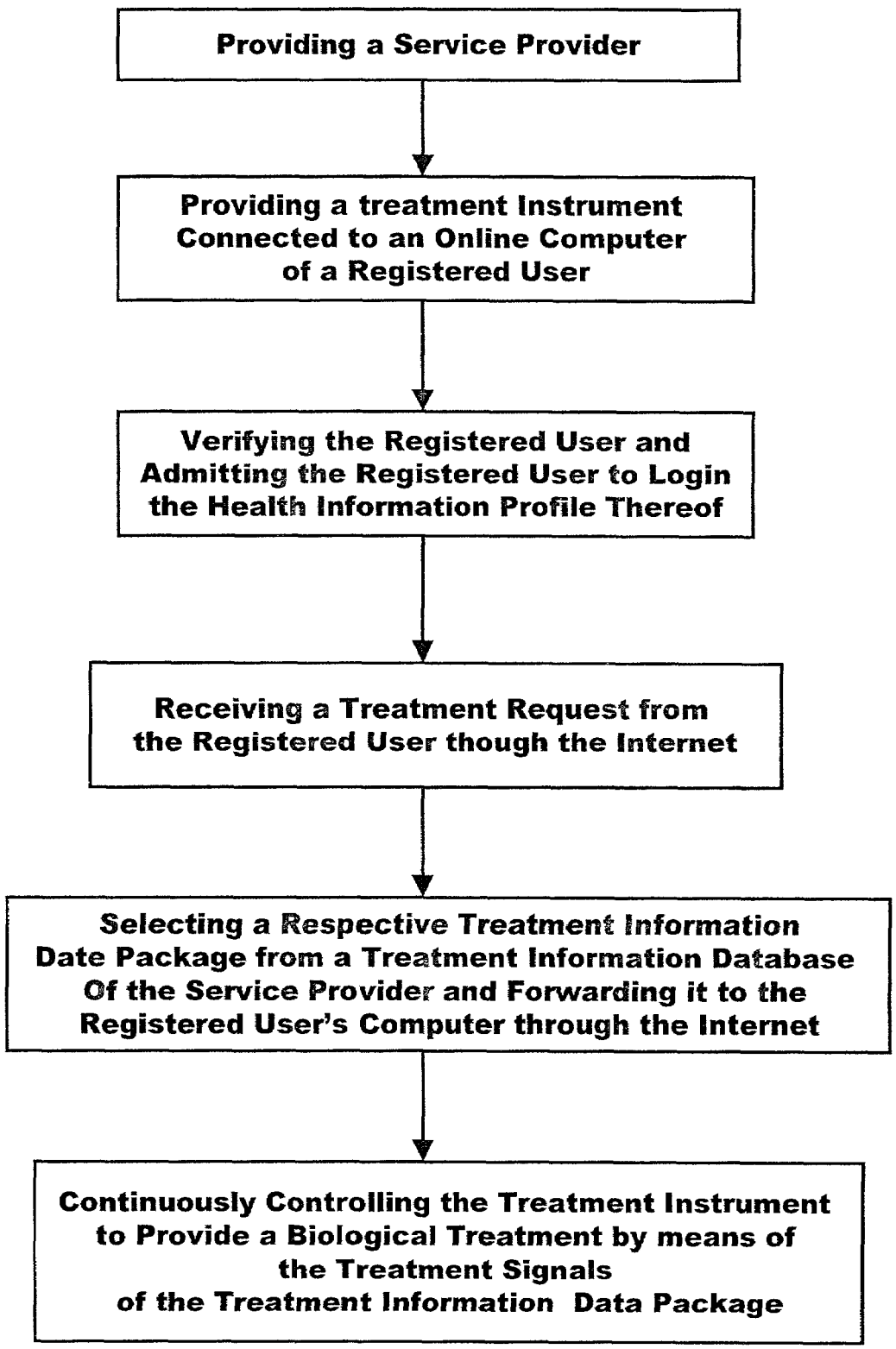
FIG. 1 is a block diagram illustrating a distance-treatment through public network according to a preferred embodiment of the present invention.

Referring to the drawings, the present invention relates to a method and system of distance-treatment through public network, which comprises the following steps:

(a) Provide a treatment information database and a health information database for a service provider 10, wherein the treatment information database includes a plurality of treatment information with respect to different kinds of classified health problem and the health information database includes health information profiles established for registered users respectively, wherein each of the health information profiles includes a personal general information and a personal health information of the respective registered user.

(b) Provide a treatment instrument 40 connected with an information connection system 20 of the respective registered user, wherein the information connection system 20 is arranged to be capable of communicating with the service provider 10 through a public network 30.

(c) Verify the registered user and admit the registered user to login the health information profile of the registered user and to request a distance-treatment.

(d) Receive a treatment request from the information connection system 20 of the registered user through the public network 30.

(e) Based on the treatment request and the health information profile of the registered user, select a treatment information data package from the treatment information database and send digital treatment signals of the treatment information data package to the information connection system 20 of the registered user through the public network 30.

(f) Decode the digital treatment signals received into analog treatment signals which are sent to the treatment instrument 40 to program and control the treatment of the registered user.

Due to the rapid development of the communication tools, patient can obtain a diagnosis without physically interviewing the doctor. A patient can take a blood test in a laboratory or have an X-ray test in an X-ray clinic and then send the blood test report or the X-ray film to the doctor. Thereafter, the patient can contact the doctor through a communication tool such as a telephone network and obtain a diagnosis. A medical center or a physician clinic can be networked with all its member patients to provide diagnosis through a private communication network.

The most common public network is the Internet, which is a data transmission network connecting all networked information connection systems (i.e. the computers) together, through which everyone in the world is allowed to communicate with another. Through the Internet, the visual images, graphic images, audio sounds, and writing data, which are coded as digital data by the computer, can be transmitted from place to place instantaneously. Through the Internet, a computer can be continuously connected with another computer for data transmission, such as emailing and logging on a web site. Also, though the Internet, a computer can control and operate another online computer anywhere in the world.

By means of the Internet, patients are capable of interviewing their physicians to obtain a diagnosis and even a prescription. Medical web sites are available all over the world. However, no one can receive biological treatment without physically visiting the physician or the health consultant. Therefore, although the present invention may also provide a diagnosing step to provide diagnosis, how to obtain a diagnosis is not the primary subject matter of the present invention that the main issues are to give biological treatment through the public network such as the Internet and to control the biological treatment through the Internet.

Figure 2:
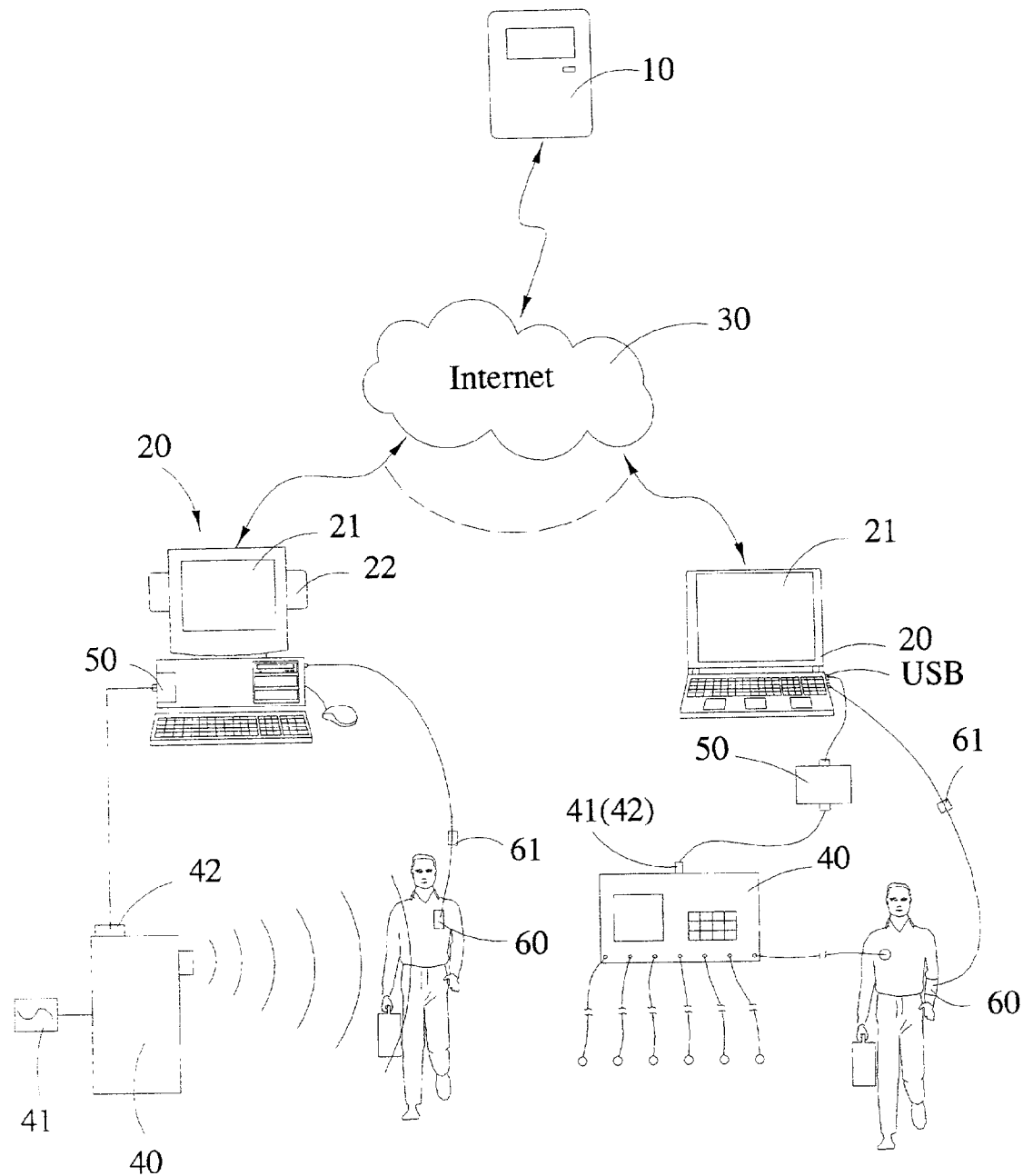
FIG. 2 is a schematic view of a distance-treatment system providing the distance-treatment through Internet according to the above preferred embodiment of the present invention.

Accordingly, as shown in FIG. 2, the system of distance-treatment through public network according to the preferred embodiment of the present invention comprises the service provider 10 which is embodied as a web server operated by an enterprise such as a commercial corporation, a medical center or a non-profit organization, the information connection system 20 which is embodied as a computer adapted to be operated by the registered user, the public network 30 which is embodied as the Internet networking the computer 20 with the Internet web site 10, and at least one treatment instrument 40 electrically connected with the computer via a decoder 50.

The service provider 10, i.e. the Web Server is used to publish the web pages, provide the interface allows customer login, fill their profile and medical information, download treatment data, feedback their progress, etc. The registered user's information and treatment information are stored in the Web Server which may comprise one or more computers, in which internet server, database/LDAP server, CGI/ASP/JSP may be installed to facilitate programming and operations.

The information connection system 20 is preferred to be a personal computer, which can be in form of desk, laptop, palm, mobile phone, or other form of microcontroller. There is Internet browser equipped with the computer which allows the registered user to browse Internet.

The public network 30 is preferred to be the Internet which comprises the World Wide Web, e-mail, File Transfer Protocol, and number of other application. Here it is used as facility to provide the interface to the registered user. It allows registered user to view and fill the data on it, and download the data from it.

The treatment instrument 40 comprises a power source 41 and an information input connection 42. The power source 41 can be batteries installed therein or an external inlet for electrically connecting to an AC wall socket. The information input connection 42 is a data inlet port adapted to be connected to a data outlet port of the computer 20 by a data bus. The treatment instrument 40 may simply include a USB connection which is a combination of the power source 41 and the information input connection 42. The USB connection is connected to any USB port of the computer 20, so that the treatment instrument 40 can receive both the electrical power supply and corresponding information from the computer 20.

As described in the background of the present invention, all sense organs and the acupoint system of a human being are "input devices" or "receivers" of the human body that can receive treatments. When appropriate treatment is applied to the predetermined "input device" of a human body, corresponding healing effects will be achieved to improve the user's health condition. Of course, if a wrong "input device" of a human body receives wrongful stimulation, adverse effects may be caused. Therefore, specific control and manage of the treatment are preferred to be carried during the treatment.

Depending on what kind of treatments is required, the treatment instrument 40 can be a visual signal producer, an audio signal producer, an electrical acupuncture device, an far-infrared emitting device, a bio-energizer which is an instrument generating radio waves or electromagnetic waves with specific ranges of wavelength and frequency, a heater, a magnetic acupuncture device, a magnetic health treatment device, an electric massager, a massage chair or bed, and etc. In other words, all kinds of health treatment device or medical treatment device can be used as the treatment instrument 40. Even the monitor and the speakers of the computer itself can be functioned as the treatment instrument 40.

In the step (a), all users are required to be registered as registered users, each of which is requested to set up a health information profile in the health information database of the provider service 10 by inputting the user's personal general information and personal health information. The personal general information of each registered user should include the registered user's name, address, phone number, facsimile number, IP address, email address(es) for email, instant messenger and voice messenger with or without web images, age, sex, and etc. In order to register as a registered use, each user must also complete a health information questionnaire to inform personal health information including basic information such as body weight, height, fat index, eyesight record (e.g. short-sight or long-sight), heart beat per minute, blood pressure, disease history, and medical treatment history (if known). The registered user also needs to inform whether he or she has any food and medicine allergy. To complete the registration, the user should register a specific user ID and a password before the service provider 10. For security reason, the service provider 10 will also assign a different passcode to each registered user.

The registered users are classified into a general health group of registered users who merely need a general health-type distance-treatment from the service provider 10 through the Internet 30 and a specific medical group of registered users who need a specific medical-type distance-treatment from the service provider 10 through the Internet 30.

If any general group of registered users want to upgrade to the medical group of registered users, they are requested to further provide their personal health information with their body test records. If a registered user has a recent body test record (such as within three months), the registered user can send in a verified copy thereof to the service provider 10 or, alternatively, the registered user can authorize the service provider 10 to apply a verified copy from the test clinic that the registered user made the body test. If the registered user do not have a recent body test report, the registered user is required to visit a hospital or clinic authorized by the service provider 10 to do a body test which may include, for example, a blood test, a urine test, an eyesight test, a neurology test, a dental test, and etc.

A medical group registered user may request the service provider 10 to make a diagnosis for him or her to determine whether the registered user is suffering a disease, wherein the service provider 10 will appoint a doctor or an oriental doctor, according to the selection of the registered user, to diagnose the registered user based on his or her health information profile including his or her personal general information and personal health information and provide a subject diagnosis which is recorded in the respective registered user's personal health information.

Practically, the health information profile of the registered user further comprises a diagnosis file to record his or her personal diagnosis information. The subject diagnosis made by the service provider 10 for the registered user is recorded in the diagnosis file and transferred into electronic diagnosis data to form a specific diagnosis code which is assigned to a specific disease with respect to a specific class of health condition of a patient by the service provider 10.

Preferably, the registered user is preferred to physically interview his or her doctor to obtain his or her updated diagnosis. Then, the registered user can authorize his or her doctor to login his or her own health information profile in the service provider 10 by entering his or her user ID, password and passcode and input the his or her diagnosis into his or her diagnosis file, where his or her input diagnosis will also be transferred into electronic diagnosis data to form a specific diagnosis code which is assigned to a specific disease with respect to a specific class of health condition of a patient by the service provider 10.

In the step (a), after a user completes the registration to become a registered user, the service provider 10 provides at least a suggest treatment instrument 40 for the registered user to install. For the best treatment effect, the registered user is preferred to install all the treatment instruments 40 suggested by the service provider 10. After the selection of the registered user, the service provider 10 will ship the purchased treatment instruments 40 to the registered user as soon as possible.

In the step (b), after the registered user successfully installed each treatment instrument 40, the registered user must register the treatment instrument 40 in the service provider 10 which will make a corresponding record in the health information profile of the registered user. When the registered user owns more than one treatment instruments 40, the service provider 10 should automatically detect whether all treatment instruments 40 are correctly installed and ready to function.

It is worth to mention that if the treatment instrument 40 is an analog device, the decoder 50 is required to connect between the treatment instrument 40 and the computer 20. The data loaded from the computer 20 is in form of digital. The decoder 50 comprises an interface to the computer 20, a digital-analog converter (DAC), a filter and amplifier. The decoder 50 can be in an internal decoder built in the treatment instrument 40 or an external decoder independently and physically connected between the treatment instrument 40 and the computer 20. The external decoder 50 is connected to the computer 20 via serial and parallel port.

Moreover, the decoder 50 can also be made as an internal decoder installed in the computer 20 and provide the data outlet port to be connected to the information input connection 42 of the treatment instrument 40. The internal decoder 50 for computer 20 can be in form of PC card which plug in PCI/ISA bus or embedded in main board of PC and microcontroller.

As mentioned above, even the computer 20 itself can be a treatment instrument 40 through its monitor 21 and speakers 22. Therefore, it is not a mandatory procedure for the registered user to purchase any treatment instrument 40, the registered user may merely select to use the computer 20 as the treatment instrument 40 to receive the digital treatment signals from the service provider 10. Some specific medical or health treatments require specific treatment instruments 40 to execute and perform better effects. Therefore, the service provider 10 provides a treatment instrument vs. treatment chart to illustrate what kinds of treatment can the treatment instruments provided respectively. For some diseases, more than one treatment instruments can provide healing treatments. Then the registered user may select the one he or she prefers. Also, for some diseases, more than one treatment instruments are preferred to work together in order to achieve the best result.

In the step (a), the treatment information database includes the plurality of treatment information with respect to different kinds of classified health problem and diseases. With respect to different treatment instruments 40, the treatment information is stored as the different treatment information data packages. In the step (c), the registered user must login his or her member page in the service provider 10 through the Internet 30 by entering his user ID, password and passcode in order to access his or her own health information profile and request for the distance-treatment from the service provider 10. The step (c) further comprises the steps of:

(c-1) getting the registered user's login request;
(c-2) sending a login page to the registered user's computer 20 to collect the registered user's user ID, password and passcode;
(c-3) authorizing the received the user ID, password and passcode from the registered user by checking against all the personal general information of the health information profiles of the health information database; and
(c-4) sending the member page to the registered user when the user is verified as the registered user in record, wherein the member page is a tailored web-pages for allowing the registered user to access and amend the health information profile thereof, informing the current health condition of the registered user based on the health information profile of the registered user, providing list of health problems and diseases of the registered user, and placing the treatment request.

After the verification of the registered user in the step (c), the service provider 10 recognizes the registered user and admits the registered user to make the treatment request to the service provider 10 at his or her computer 20 through the Internet 30 as described in the step (d). In responsive to the registered user's treatment request, the service provider 10 sends the respective registered user a treatment page which may include the list of the health problems and diseases that the registered user suffers, treatment opinions from doctors, recommendation of beneficial foods and activities for each of the listed health problems and diseases of the registered user, recommended biological treatments with respect to the listed health problems and diseases that the registered user suffers respectively, and information of suggested treatment instrument for executing each recommended biological treatment.

In the step (d), the recommended biological treatments to be listed can be limited to those treatments that can be processed by the specific treatment instrument 40 owned by the registered user. Alternatively, all possible recommended biological treatments regarding all the health problems and diseases of the registered user are still provided with the illustration of the specific treatment instrument 40 required by each recommended medical or health treatment, so as to remind the registered user that there are respective treatments available for a particular health problem or disease of the registered user so that the registered user may reconsider whether he or she wants to additional own the corresponding treatment instrument 40.

After placing the treatment request, the registered user is then admitted to select the specific treatment information data package for his or her treatment instrument 40, wherein the step (e) further comprises the steps of:

(e-1) enabling the registered user to select the particular health problem or disease to be treated (from the list of the health problems and diseases that the registered user suffers);

(e-2) enabling the registered user to select the specific recommended biological treatment with respect to the selected health problem or disease;

(e-3) calling the personal general information and personal health information of the health information profile of the registered user from the health information database to reference the specific recommended biological treatment selected by the registered user in the step (e-2);

(e-4) selecting, by the service provider 10, the most appropriate treatment information data package from the treatment information database regarding to the selected recommended biological treatment and the health information profile of the registered user, wherein the treatment information data package contains the digital treatment signals adapted for controlling the specific treatment instrument 40 connected to the computer 20 of the registered user; and (e-5) sending the treatment information data package to the computer 20 of the registered user through the Internet 30 so as to transmit the digital treatment signals to the computer 20 for controlling the treatment instrument 40.

If the treatment instrument 40 is the computer 20 itself, the digital treatment signals received in the computer substantially controls the computer 20 to produce predetermined visual and audio messages. For example, for a registered user having a manic-depressive psychosis, the registered user may select the manic-depressive psychosis as the health problem to be treated in the step (e-1) and select the visual and audio health treatment as the biological treatment correspondingly in the step (e-2). Then, for example, the registered user may receive the respective treatment information data package which contains both visual and audio digital treatment signals to display a specific films in the monitor 21 and broadcasting a specific music through the speakers 22 of the computer 20.

However, if the treatment instrument 40 is an independent analog treatment instrument connected to the computer 20, the digital treatment signals received in the computer 20 must be decoded before the treatment instrument 40 recognizes the signals. Therefore, the step (f) is necessary for decoding the digital treatment signals received in the computer 20 into analog treatment signals which are then sent to the treatment instrument 40 to program and control the treatment of the registered user.

For example, if the treatment instrument is an electromagnetic wave generator adapted for generating electromagnetic waves with predetermined range of frequency, varies from 1 Hz to 530,000 Ghz (gigahertz), and intensity, varies from 1 mV to 10 mV, the digital treatment signals of the treatment information data package received in the computer 20 must be decoded into analog treatment signals for controlling the electromagnetic wave generator to generate electromagnetic waves with a predetermined frequency and intensity for a certain period of time with respect to different health problems and diseases for a patient having different general health condition.

For example, if the registered user is a mid-age mother having a neuroticism problem, she may select a health treatment for a select disease called "neuroticism". Then a specific treatment information data package is sent from the service provider 10 through the Internet 30 to the computer 20, wherein the digital treatment signals of the treatment information data package are decoded by the decoder 50 and sent to the electromagnetic wave generator, i.e. the treatment instrument 40, for controlling it to generate electromagnetic waves having a predetermined frequency and intensity that are proved to have a sedative effect for the neuroticism. The electromagnetic waves generated can be sent to the registered user in form of lines touched to the registered user's body or put around the registered user in order to form an environment of bionics field for the registered user.

For example, if the treatment instrument is an electrical acupuncture device comprising a plurality of terminal pads adapted to attach on the human acupoints, wherein through the terminal pads, electrical pulses with predetermined frequency and intensity are generated to stimulate the respective acupoints for a certain period of time to achieve various healing effects.

For example, a male overweight registered user who has a high blood pressure and high cholesterol problems may select high blood pressure as his selected health problem in the step (e-1) and select a corresponding recommended biological treatment in the step (e-2). Then, the treatment information data package is sent from the service provider 10 to the computer 20 of the registered user through the Internet 30, wherein the treatment information data package contains information of the specific human acupoints which are indicated for the registered user to attach the terminal pads thereon and the digital treatment signals which is decoded by the decoder 50 to analog treatment signals to control the treatment instrument 40, i.e. the electrical acupuncture device, to produce electric pulses with predetermined frequency and intensity to stimulate the corresponding acupoints through the terminal pads for a predetermined period of time.

Furthermore, after the step (f), the present invention is preferred to comprise the additional step (g) of feeding back a responsive health information of the registered user to the service provider 10 for controlling and adjusting properties of the digital treatment signals of the treatment information data package to be sent from the service provider 10 to the computer 20 of the registered user.

According to the preferred embodiment of the present invention, the step (g) further comprises the steps of:

(g-1) detecting the current health information of the registered user after the biological treatment or during the biological treatment;

(g-2) sending the detected current health information to the computer 20 as the responsive health information;

(g-3) feeding the responsive health information back to the service provider 10 from the computer 20 through the public network 30;

(g-4) evaluating the original digital treatment signals of the treatment information data package to be sent to the computer 20 of the registered user with respect to the received responsive health information;

(g-5) if necessary, adjusting the digital treatment signals of the treatment information data package to modified treatment information data package which contains updated digital treatment signals; and (g-6) sending the modified treatment information data package to the computer 20 of the registered user through the Internet 30 so as to transmit the updated digital treatment signals to the computer 20 to update the control of the treatment instrument 40.

In the step (g-1), a detector 60, which is electrically connected with the computer 20 in a way similar to the connection of the treatment instrument 40 with the computer 20, can be used to detect current health data as the responsive health information to be fed back to the service provider 10. The detector 60, for example, can be a heart beat detector or blood pressure measurer. Similarly, when the responsive health information detected are analog signals, a decoder 61 including an analog-digital converter (ADC) is needed to connected between the computer 20 and the analog detector 60, so that the analog responsive health information can be converted into corresponding digital responsive health information for transmitting back to the service provider 10 through the Internet.

When the responsive health information is continuously detected during the biological distance-treatment of the present invention, the current health information will be continuously feeding back to the service provider 10 so as to render the biological treatment becoming a live-treatment that the digital treatment signals of the treatment information data package can thus be controlled and adjusted correspondingly through the Internet so as to provide a better and more effective treatment result. In other words, the frequency and intensity of the electromagnetic of the electromagnetic wave generator or the electric pulses of the electrical acupuncture device can thus be controlled and adjusted in responsive to the current health condition of the registered user who is receiving the distance-treatment.

For some other general health treatments, the responsive health information of the registered user in the step (g) is obtained by requesting the registered user to input his or her health information including his or her feeling, progress and symptom so as to control and adjust the digital treatment signals of the treatment information data package to be sent from the service provider 10 to the computer 20 of the registered user.

In view of above, the biological distance-treatment through public network of the present invention substantially achieves the following features and advantages:

(1) The present invention provides a biological distance-treatment through public network which enables a registered user to receive biological treatment at his or her own place under the professional instruction.

(2) The treatment instrument of the user is directly controlled by the Web Server of the service provider through the Internet according to the diagnosis provided by the user or the personal health condition inputted by the registered user, and thus the registered user can receive health treatment at home or even during business hours whenever the registered user's computer connected with the treatment instrument is online, so that the registered user saves the time to make appointment and see the doctor at specific time. This is especially true for those who have been suffering chronic illness.

(3) Live-reaction information of the user during treatment is fed back to the service provider through the public network so that the service provider may adjust the registered user's treatment instrument through the public network correspondingly.

(4) The registered users can receive respective medical treatment at the user's own place after the user inputs his or her medical diagnosis through the public network.

(5) Different registered users who registered with different passwords and user IDs can use the same information connection system and treatment instrument to receive different treatments.

What is claimed is:

1. A method of providing distance-treatment for registered users through Internet, comprising the steps of:

(a) establishing an information connection system comprising a computer, a visual signal producer and an audio signal producer, wherein said information connection system is arranged to be capable of communicating with a service provider through said Internet;

(b) requiring said registered user to login said service provider through said Internet, wherein each of said registered user is able to present a diagnosis record and a health information profile for said information connection system;

(c) communicating a treatment request to said information connection system on the basis of said diagnosis record of said registered users through said Internet, wherein after said verification of said registered user, said service provider recognizes said registered user and admits said registered user to make said treatment request to said service provider at said information connection system through said Internet, wherein in responsive to said treatment request of said registered user, said service provider sends said service provider sends said respective registered user a treatment page which includes a list of said health problems and diseases that said registered user suffers, treatment opinions from doctors, recommendation of beneficial foods and activities for each of said listed health problems and diseases of said registered user, recommended biological treatments with respect to said listed health problems and diseases that said registered user suffers respectively, and information of suggested treatment instrument for executing each recommended biological treatment;

(d) based on said treatment request and said health information profile for said registered user, formulating a treatment information data package from a treatment information database provided by said service provider;

(e) commanding said computer to perform treatment by digital treatment signals based on said treatment information data package, wherein said treatment is initiated and operated by said information connection system on said registered user, wherein said treatment is selected from a group consisting of an audio and visual treatment to said registered user via said audio device and said monitor respectively, and is based on said treatment data package, wherein said digital treatment signals are decoded into analog treatment signals which are sent to said computer to program and control said treatment of said registered user with said treatment instrument; and (f) sending a responsive health information of said registered user to the service provider for controlling and adjusting properties of said digital treatment signals of said treatment information data package; and (g) communicatively connecting a second treatment instrument with said information connection system, wherein said second treatment instrument further includes at least one addition treatment option as an additional treatment for said registered user apart from said audio and visual treatment.

2. The method, as recited in claim 1, further comprising a step, before said step (a), of establishing said treatment information database and a health information database for said service provider, wherein said treatment information database includes a plurality of treatment information with respect to different kinds of classified health problem, wherein said health information database includes said health information profiles established for said registered users respectively, wherein each of said health information profiles includes a personal general information and a personal health information of said respective registered user.

3. The method, as recited in claim 2, wherein said personal general information includes a specific user ID and a specific password registered by each of said registered users and a specific passcode assigned to each of said registered users by said service provider.

4. The method, as recited in claim 3, wherein said personal health information of each of said registered users includes personal physical information and a recent body test record of said respective registered user, and said health information profile of each of said registered users further comprises a diagnosis file recording a personal diagnosis information of said respective registered user.

5. The method, as recited in claim 4, wherein the step (a) further comprises a step of registering said treatment instrument in said service provider so as to make a corresponding record in said health information profile of said respective registered user.

6. The method, as recited in claim 5, wherein said step (b) comprises the steps of:
   (b-1) receiving a login request from said information connection system of said registered user;
   (b-2) sending a login page to said information connection system of said registered user to collect said user ID, said password and said passcode of said respective registered user;
   (b-3) authorizing said received user ID, password and passcode from said registered user by checking against all said personal general information of said health information profiles of said health information database; and
   (b-4) sending said member page to said registered user when said user is verified as said registered user in record, wherein said member page is a tailored webpages for allowing said registered user to access and amend said health information profile thereof, informing said current health condition of said registered user based on said health information profile of said registered user, providing list of health problems and diseases of said registered user, and placing said treatment request.

7. The method, as recited in claim 6, wherein said step (d) comprises the steps of:
   (d-1) selecting said particular health problem and disease to be treated from said list of said health problems and diseases by said registered user;
   (d-2) enabling said registered user to select said specific recommended biological treatment with respect to said selected health problem or disease as said primary treatment;
   (d-3) calling said personal general information and personal health information of said health information profile of said registered user from said health information database to reference said specific recommended biological treatment selected by said registered user;
   (d-4) selecting, by said service provider, said specific treatment information data package from said treatment information database regarding to said selected recommended biological treatment and said health information profile of said registered user, wherein said treatment information data package contains said digital treatment signals adapted for controlling said specific treatment instrument connected to said information connection system of said registered user; and
   (d-5) sending said treatment information data package to said information connection system of said registered user through said Internet so as to transmit said digital treatment signals to said information connection system for controlling said treatment instrument.

8. The method, as recited in claim 7, wherein said step (f) comprises the steps of:
   (f-1) detecting current health information of said registered user during said biological treatment;
   (f-2) sending said detected current health information to said information connection system as said responsive health information through said Internet;
   (f-3) feeding said responsive health information back to said service provider from said information connection system through said Internet;
   (f-4) evaluating said digital treatment signals of said treatment information data package sent to said information connection system of said registered user with respect to said received responsive health information;
   (f-5) adjusting said digital treatment signals of said treatment information data package to modified treatment information data package which contains updated digital treatment signals; and
   (f-6) sending said modified treatment information data package to said information connection system of said registered user through said Internet so as to transmit said updated digital treatment signals to said information connection system to update said control of said computer such that said current health information is continuously feeding back to said service provider so as to render said biological treatment becoming a live-treatment that said digital treatment signals of said treatment information data package is controlled and adjusted correspondingly through said Internet so as to provide a better and more effective primarily audio and visual treatment results.

9. The method, as recited in claim 8, wherein after said step (f-1) and before said step (f-2), said current health information detected are analog signals which are converted into digital signals of said responsive health information for transmitting back to said service provider through said Internet.

10. The method, as recited in claim 9, wherein said responsive health information of said registered user is obtained by requesting said registered user to input said responsive health information, including a feeling, progress and symptom of said registered user, so as to control and adjust said digital treatment signals of said treatment information data package to be sent from said service provider to said information connection system of said registered user.

11. The method, as recited in claim 2, wherein said step (b) comprises the steps of:
   (b-1) receiving a login request from said information connection system of said registered user;
   (b-2) sending a login page to said information connection system of said registered user to collect said user ID, said password and said passcode of said respective registered user;
   (b-3) authorizing said received user ID, password and passcode from said registered user by checking against all said personal general information of said health information profiles of said health information database; and
   (b-4) sending said member page to said registered user when said user is verified as said registered user in record, wherein said member page is a tailored webpages for allowing said registered user to access and amend said health information profile thereof, informing said current health condition of said registered user based on said health information profile of said registered user, providing list of health problems and diseases of said registered user, and placing said treatment request.

12. The method, as recited in claim 11, wherein said step (d) comprises the steps of:
- (d-1) selecting said particular health problem and disease to be treated from said list of said health problems and diseases by said registered user;
- (d-2) enabling said registered user to select said specific recommended biological treatment with respect to said selected health problem or disease as said primary treatment;
- (d-3) calling said personal general information and personal health information of said health information profile of said registered user from said health information database to reference said specific recommended biological treatment selected by said registered user;
- (d-4) selecting, by said service provider, said specific treatment information data package from said treatment information database regarding to said selected recommended biological treatment and said health information profile of said registered user, wherein said treatment information data package contains said digital treatment signals adapted for controlling said specific treatment instrument connected to said information connection system of said registered user; and
- (d-5) sending said treatment information data package to said information connection system of said registered user through said Internet so as to transmit said digital treatment signals to said information connection system for controlling said treatment instrument.

13. The method, as recited in claim 12, wherein said step (f) comprises the steps of:
- (f-1) detecting current health information of said registered user during said biological treatment;
- (f-2) sending said detected current health information to said information connection system as said responsive health information through said Internet;
- (f-3) feeding said responsive health information back to said service provider from said information connection system through said Internet;
- (f-4) evaluating said digital treatment signals of said treatment information data package sent to said information connection system of said registered user with respect to said received responsive health information;
- (f-5) adjusting said digital treatment signals of said treatment information data package to modified treatment information data package which contains updated digital treatment signals; and
- (f-6) sending said modified treatment information data package to said information connection system of said registered user through said Internet so as to transmit said updated digital treatment signals to said information connection system to update said control of said computer such that said current health information is continuously feeding back to said service provider so as to render said biological treatment becoming a live-treatment that said digital treatment signals of said treatment information data package is controlled and adjusted correspondingly through said Internet so as to provide a better and more effective primarily audio and visual treatment results.

14. The method, as recited in claim 13, wherein after said step (f-1) and before said step (f-2), said current health information detected are analog signals which are converted into digital signals of said responsive health information for transmitting back to said service provider through said Internet.

15. The method, as recited in claim 14, wherein said responsive health information of said registered user is obtained by requesting said registered user to input said responsive health information, including a feeling, progress and symptom of said registered user, so as to control and adjust said digital treatment signals of said treatment information data package to be sent from said service provider to said information connection system of said registered user.

* * * * *